US00PP33929P2

(12) United States Plant Patent
Horvath

(10) Patent No.: US PP33,929 P2
(45) Date of Patent: Feb. 1, 2022

(54) ***ANDROPOGON GERARDII* PLANT NAMED 'HOLY SMOKE'**

(50) Latin Name: *Andropogon gerardii*
Varietal Denomination: Holy Smoke

(71) Applicant: Brent Arpad Horvath, Fontana, WI (US)

(72) Inventor: Brent Arpad Horvath, Fontana, WI (US)

( * ) Notice: Subject to any disclaimer, the term of this patent is extended or adjusted under 35 U.S.C. 154(b) by 0 days.

(21) Appl. No.: 16/974,330

(22) Filed: Jan. 4, 2021

(51) Int. Cl.
*A01H 5/12* (2018.01)
*A01H 6/46* (2018.01)

(52) U.S. Cl.
USPC ..... Plt./384

(58) Field of Classification Search
USPC ..... Plt./384
See application file for complete search history.

*Primary Examiner* — Susan McCormick Ewoldt
*Assistant Examiner* — Karen M Redden

(57) ABSTRACT

A new, distinct *Andropogon gerardii* plant as illustrated and described, characterized by an upright plant with a height of 190 cm, blue-green colored foliage with red stems, and purple fall color.

1 Drawing Sheet

Figure 1:
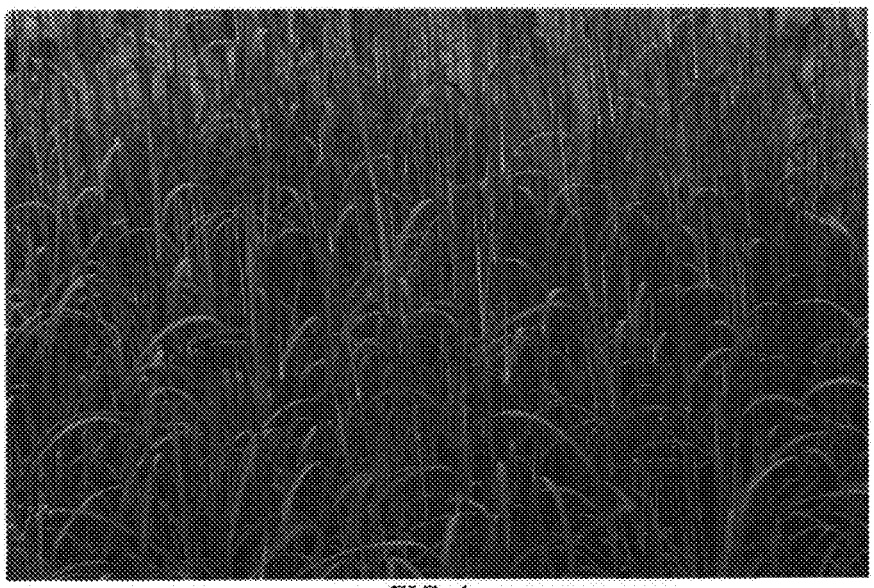

Latin name: *Andropogon gerardii.*
Cultivar name: 'Holy Smoke'.

BACKGROUND OF THE INVENTION

The present invention relates to a new form of *Andropogon gerardii* plant named 'Holy Smoke'. 'Holy Smoke' is a seedling of *Andropogon gerardii* 'Blackhawks', U.S. Plant Pat. No. 27,949, characterized by a height of 190 cm, blue-green colored foliage with red stems, and purple fall color, compared to dark green colored foliage and the shorter habit of 150 cm of the parent plant. The new plant was grown as a seedling of *Andropogon gerardii* 'Blackhawks', U.S. Plant Pat. No. 27,949, by the inventor at a wholesale perennial nursery in Hebron, Ill. USA in 2017. The selection of this plant was due to its height of 190 cm, and blue-green colored foliage with red stems, and purple fall color. Asexual, vegetative division propagation has been the only means of reproduction. Initial vegetative propagation has taken place at Hebron, Ill. since 2018. In 2019 we planted 200 plants. To date these plants have remained uniform in height, and foliage color. The new *Andropogon gerardii* has shown to be stable and identical in reproduction to the parent after making over 700 vegetative divisions from 2018 to 2020. No plants of *Andropogon gerardii* 'Holy Smoke' have been sold in this country, or anywhere in the world, prior to the filing of this application, nor has any disclosure of the new plant been made prior to the filing of this application with the exception of that which was disclosed by the inventor and his nursery in Hebron, Ill. US within one year of the filing of this application and was either derived directly or indirectly from the inventor.

SUMMARY OF THE INVENTION

In the following description, color references are made to The Royal Horticultural Society Colour Chart (copyright 2001). The new *Andropogon gerardii* plant named 'Holy Smoke' has shown the characteristics of a more upright plant with a height of 190 cm, blue-green colored foliage with red tips and joints, and purple fall color to be unique and stable. For purpose of the comparison the new plant will be referred to as 'Holy Smoke'.

Plants of 'Holy Smoke' can be compared to plants of *Andropogon gerardii* 'Blackhawks', U.S. Plant Pat. No. 27,949. 1. 'Holy Smoke' has an upright growth and a height of 190 cm compared to the height of *Andropogon gerardii* 'Blackhawks' which has an average height of 150 cm. 2. 'Holy Smoke' has a foliage color of blue-green 146 A coloring to 187 A compared to *Andropogon gerardii* 'Blackhawks' which has foliage color of 147 A coloring to N186 A.

Plants of 'Holy Smoke' can be also be compared to plants of *Andropogon gerardii* 'Red October', U.S. Plant Pat. No. 26,283. 1. The 'Holy Smoke' has a height of 190 cm compared to the height of *Andropogon gerardii* 'Red October' which has an average height of 130-150 cm. 2. The new *Andropogon* has a foliage color of blue-green 146 A coloring to 187 A compared to *Andropogon gerardii* 'Red October' which has foliage color that is, RHS 147 A coloring to N92 A and eventually close to 187 C.

Plants of 'Holy Smoke' can be also be compared to plants of *Andropogon gerardii* 'Dancing Wind', U.S. Plant Pat. No. 26,892. 1. The 'Holy Smoke' has a height of 190 cm compared to the height of *Andropogon gerardii* 'Dancing Wind' which has an average height of 140-170 cm. 2. The new *Andropogon* has a foliage color of blue-green 146 A coloring to 187 A compared to *Andropogon gerardii* 'Dancing Wind', which has foliage color of yellow-green N144 A coloring to 183 D.

DESCRIPTION OF PHOTOGRAPHS

FIG. 1. Shows a 2 year old plant in August with red stems in Hebron, Ill. USA.

Figure 2:
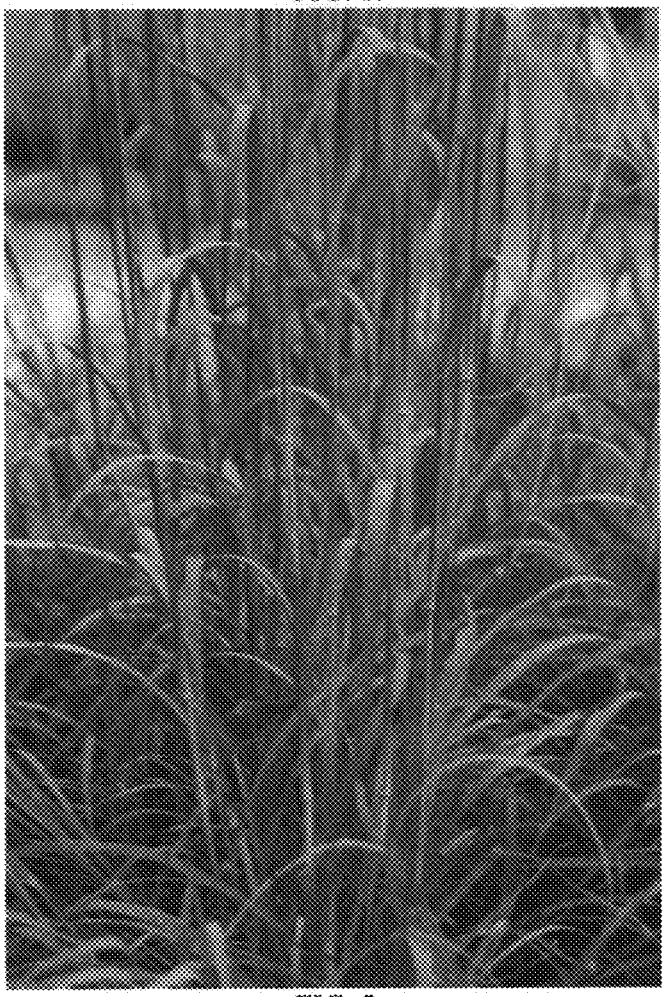

FIG. 2. Shows a 2 year old plant in September with fall foliage color in Hebron, Ill. USA.

DETAILED BOTANICAL DESCRIPTION

In the following description, color references are made to The Royal Horticultural Society Colour Chart 2001. The plant herein described is an established 2 year old plant growing in a garden, grown in full sun and irrigated in Hebron, Ill. USA. Measurements and numerical values represent averages of typical plants.

Botanical classification: *Andropogon gerardii* plant named 'Holy Smoke'.

Parentage: Female: An open pollinated *Andropogon gerardii* 'Blackhawks'. Male: an unnamed and unknown *Andropogon gerardii.*

Propagation: Vegetative division.

Plant description: Overall habit of the new *Andropogon* is clumping with upright culms topped by red colored flowers beginning in August. Vigor is moderate.

*Plant height.*—190 cm.

*Plant width.*—60 cm.

Foliage and stems:

*Foliage description.*—Glabrous, flat blade, sheathed from node of attachment to ligule, linear.

*Type.*—Deciduous, grass growing in culms.

*Shape.*—Linear.

*Sheath.*—1 cm wide, 12 cm long, surface — glabrous.

*Ligules.*—Up to 1-2 mm long and less than 1 mm wide.

*Number of blades.*—Typically 6 blades per stem.

*Blade length.*—10 mm wide, up to 46 cm long, average 35 cm without the sheath.

*Adaxial leaf description.*—Leaf color is 146 A coloring up to N187A.

*Abaxial leaf description.*—Leaf color is 146 A with N189 C coloring up to 186A.

*Veins.*—Parallel, same color as surrounding leaf on both top and bottom of leaf.

*Culm description.*—Erect, cylindrical, typically with 6 leaves.

*Culm or stem diameter.*—5 mm average, but typically 4 mm between the nodes and swelling to 6 mm at the base of the internodes.

*Number of culms or stems per clump.*—Over 30.

*Culm color ranges.*—185 B & C below nodes.

*Node description.*—Cylindrical.

*Number of nodes per culm.*—Average 6.

*Length of internodes.*—Ranges from 12 cm.

Flower inflorescence:

*Inflorescence type.*—Terminal raceme with sessile and pedicillate spikelets.

*Rachis.*—1 mm wide and up to 17 cm long, color starts 146 A coloring to N187 B.

*Overall raceme size.*—4 cm wide, 13 cm long.

*Rames.*—Mostly 4 mm wide, 9 cm long.

*Rachilla.*—Less than 1 mm wide, 8 mm long, color starts 146 A coloring to 187 B.

*Inflorescence color.*—As a whole the color is N187 A.

*Spikelet.*—Sessile and pedicellate — Both 4 mm wide 9 cm long, color is N187 A.

*Individual floret size.*—2 mm wide, 12 mm long including awn.

*Lower glume.*—1-2 mm wide, 12 mm long, color starts 146 A coloring to N187 A.

*Lemma.*—Outer and inner — both, wider than 1 mm less than 2 mm, 15 mm long, color starts 146 A coloring up to N187 A.

*Awn size.*—Is more than 1 mm wide and average 10 mm long.

*Pedicels.*—4 to 5 per, rames and are shorter toward the base of the plant, 1 mm wide and 5-9 cm long.

*Flower number.*—Approximately 34 florets per rames, average 100 per spikelet, mature spikelet measuring 4 cm wide, 13 cm long.

*Cynocium.*—Stigma — 2. color close to N187 A.

*Androecium.*—Anthers — number 3, color — is orange.

*Anther size.*—2-4 mm long by 1 mm wide.

*Fertility.*—Fertile with 3 Anthers and 3 Stamens.

*Blooming habit.*—Terminal raceme on up to 190 cm stems.

*Bloom period and duration.*—Last two weeks of August to the end of September.

*Bloom color.*—N187 A.

*Fruit or seeds.*—Color is N187 A, size is 2 mm wide, 12 mm long.

*Scent.*—No scent.

*Roots.*—Stiff, fibrous, and freely branching.

*Fruit.*—Seed identical to the species except color is darker, N187 A.

*Hardiness.*—United States Department of Agriculture Zones 4-9.

*Disease resistance.*—Plants are not susceptible to any major pests or diseases.

Regarding, *Andropogon gerardii* plant named 'Holy Smoke'.

I claim:

1. A new, distinct *Andropogon gerardii* plant as illustrated and described, characterized by an upright plant with a height of 190 cm, blue-green colored foliage with red stems, and purple fall color.

* * * * *